United States Patent [19]

Konstantinova et al.

[11] 4,193,920
[45] Mar. 18, 1980

[54] AZOMETHINE DERIVATIVES OF RIFAMYCIN SV

[75] Inventors: Rumyana G. Konstantinova; Svetlana S. Zikolova; Velichka I. Apostolova; Tanya G. Toshkova, all of Sofia, Bulgaria

[73] Assignee: DSO "Pharmachim", Sofia, Bulgaria

[21] Appl. No.: 895,399

[22] Filed: Apr. 11, 1978

[30] Foreign Application Priority Data

Apr. 15, 1977 [BG] Bulgaria .................................. 36006

[51] Int. Cl.² .......................................... C07D 491/08
[52] U.S. Cl. ............................. 260/239.3 P; 424/250
[58] Field of Search .................. 260/239.3 P; 544/382

[56] References Cited

U.S. PATENT DOCUMENTS

| 4,002,752 | 1/1977 | Crecchio et al. | 260/239.3 P |
| 4,002,754 | 1/1977 | Crecchio et al. | 260/239.3 P |

FOREIGN PATENT DOCUMENTS

1109631  4/1968  United Kingdom .............. 260/239.3 P

OTHER PUBLICATIONS

Crecchio et al., "Antimicrobial 3-Formalrifamycin SV Hydrazones", in Chem. Abs. 14972g, vol. 80, 1974.
Lancini, G. et al., "Antiviral 3(piperazinyliminomethyl)rifamysin SV derivatives", in Chem. Abs. 99, 711, vol. 76, 1972.

*Primary Examiner*—Arthur P. Demers
*Attorney, Agent, or Firm*—Karl F. Ross

[57] ABSTRACT

An antibiotic with high activity of the rifamycin class with the formula

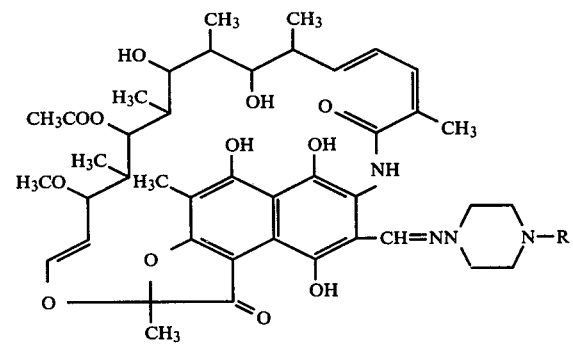

in which R is biphenylmethyl, cinnamyl or alpha-naphthylmethyl.

2 Claims, No Drawings

AZOMETHINE DERIVATIVES OF RIFAMYCIN SV

FIELD OF THE INVENTION

This invention relates to azomethine derivatives of rifamycin SV, which have a high degree of activity against gram-positive microorganisms and tubercular bacteria.

BACKGROUND OF THE INVENTION

The rifamycin family is an ancestor of a broad group of antibiotics. The most used antibiotic in medical practice is the Rifampycin (Tubocin, with formula II, which is obtained through the condensation of $N^1$-methyl-$N^4$-aminopiperazine with 3-formyl rifamycin SV (Maggi N. et al . . . Chemotherapia, 1966, 11, 285; Brit. Pat. No. 1 219 360).

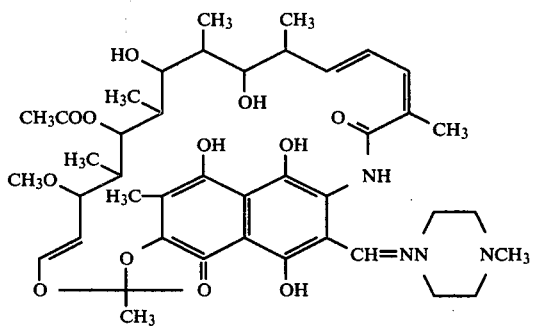

As the microorganism stability against antibiotics rapidly increases, continuous research for new antibacterial preparations is imperative.

There are also known derivatives of 3-formyl rifamycin SV with some other substituted $N^4$-aminopiperazines, which possess antibacterial, antitubercular and antivirus action (Germ. Pat. No. 2 127 172).

OBJECT OF THE INVENTION

The object of the invention is the provision of new azomethine derivatives of rifamycin SV.

DESCRIPTION OF THE INVENTION

The compounds according to the invention have the following formula

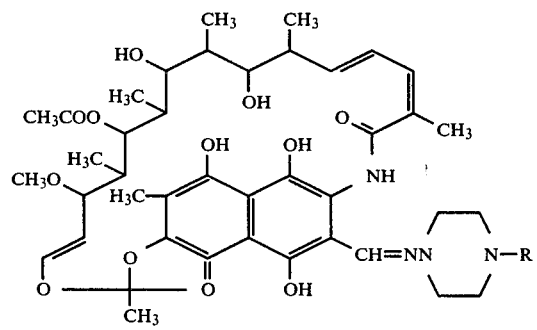

where R may denote biphenyl-methyl, cinnamyl, or α-naphthyl-methyl radical.

Compounds of the formula II are obtained according to the following general scheme:

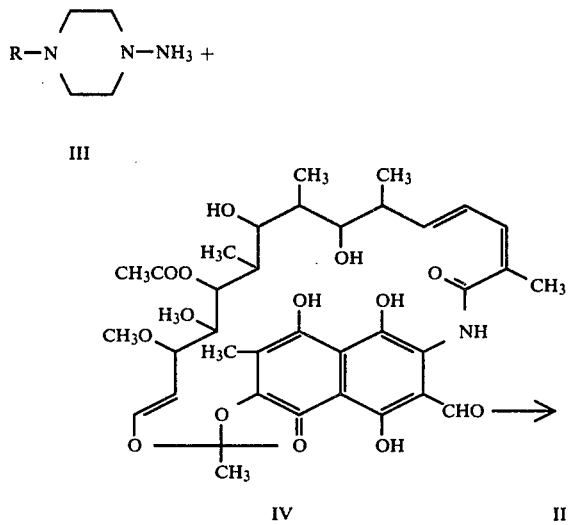

where R is as above.

Equimolar quantities of correspondingly substituted aminopiperazines (III) and 3-formyl rifamycin SV (IV) are reacted in a medium of inert solvent at ambient temperature for ½–3 hours. The product thus obtained is recrystallized.

Compounds according to the invention, when tested in vitro, showed high activity against gram-positive and gram-negative microorganisms, (e.g. higher than that of such known antibiotics as Tubocin, Ampycillin and Gentamycin).

The following examples throw more light on the invention. Example: 2.9 g (0.004 mole) of 3-formyl rifamycin SV is dissolved in 40 ml of dry tetrahydrofuran, then 0.064 g (0.004 mole) of $N^1$-(α-naphthyl-methyl)-$N^4$-aminopiperazine, dissolved in 10 ml of dry tetrahydrofuran, is added to the solution with continuous stirring. Reaction mixture is stirred for an hour at ambient temperature and thereafter is allowed to stay for a night in a refrigerator.

The dark crystalline precipitate thus formed is recrystallized from isopropanol. Yield—3.1 g (80% of theoretical); M.p. 155°–157° C. The remaining compounds of Table 1 are obtained in a similar way.

Table 1

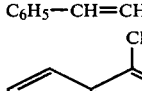

| NUMBER | R | CODE | M.P. °C. | YIELD, % |
|---|---|---|---|---|
| 1. | $(C_6H_5)_2CH-$ | T-10 | 167–168 | 73 |
| 2. | $C_6H_5-CH=CH-CH_2-$ | T-9 | 165–166 | 80 |
| 3. | (naphthyl-$CH_2-$) | T-8 | 155–157 | 80 |

The testing in vitro of the compounds' activity used the Method of step dilutions in liquid nutrious media (meat-peptonic bouillon and Sothon's semisynthetic nutrious medium). For tubercular bacteria, inoculum from Mycobacterium t.b.c. $H_{37}R_v$—a platinum loop from a month-old membrane on Sothon's medium—is employed, and for the remaining bacteria *Staphylococc. aur.u.Esch.coli* $10^4$ cells/ml. The results of research performed are summarized in Table 2.

Table 2

| COMPOUNDS AND PREPARATIONS | Activity of compounds T-8, T-9, T-10 against various species of microorganisms (mg/ml). | | | | |
|---|---|---|---|---|---|
| | MICROORGANISMS | | | | |
| | STAPHYLOC. AUREUS | ESCH. COLI | PROTEUS VULGARIS | PSEUDOM. AERUGINOSA | MYCOBACT. tbc $H_{37}R_v$ |
| T-8 | 0.007 | 25 | 12.5 | 25 | 0.07 |
| T-9 | 0.007 | 25 | 25 | 25 | 0.2 |
| T-10 | 0.15 | 25 | 25 | 25 | 0.2 |
| Tubocin | 0.2 | 25 | 12.5 | 25 | 0.2 |
| Ampycillin | 0.1 | 5 | 100 | 100 | 100 |
| Gentamycin | | 0.5 | 0.2 | 0.5 | 100 |

T-8 compound exhibits in vitro activity against *Staphiloc. aureus* in minimum repressive concentration of 0.007 μg/ml, and that for Tubocin is of the same values. T-8 activity against Mycobacterium t.b.c. $H_{37}R_v$ is higher than that for Tubocin (0.07 resp. 0.2). T-8 activity against gram-negative microorganisms of *Esch. coli, Pseudom. aerug., Proteus vulgaris* I, is similar to that of Tubocin (minimum repressive concentration 12.5–25 μg/ml).

The acture toxicity of the T-8 compound is tested on white mice and is compared with that of Tubocin. At $LD_{50}=1484$ mg/kg for Tubocin, the $LD_{50}$ for T-8 is higher than 4000 mg/kg weight.

On test animals, the T-8 compound gives serum concentrations similar to that of Tubocin.

What we claim is:
1. An azomethine rifamycin SV with the formula

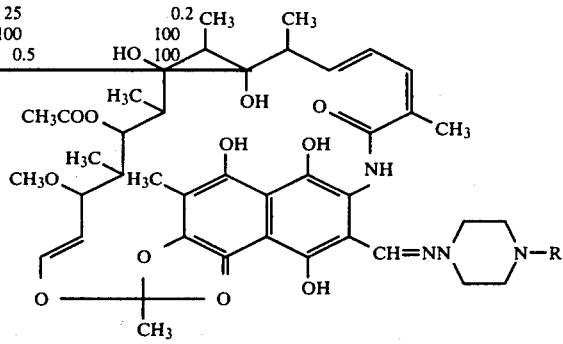

where R is biphenylmethyl, cinnamyl, or α-naphthylmethyl.

2. The compound defined in claim 1 wherein R is cinnamyl.